United States Patent [19]

Knight et al.

[11] 4,081,525

[45] Mar. 28, 1978

[54] RADIOIMMUNOASSAY OF PLASMA STEROIDS

[75] Inventors: William S. Knight, Laguna Beach; Barbara J. Kelley, Upland, both of Calif.

[73] Assignee: Beckman Instruments, Inc., Fullerton, Calif.

[21] Appl. No.: 710,499

[22] Filed: Aug. 16, 1976

[51] Int. Cl.$^2$ .................... A61K 43/00; G01N 33/16
[52] U.S. Cl. ...................... 424/1; 23/230 B; 424/12
[58] Field of Search .............. 23/230 B; 424/1, 12, 424/1.5

[56] References Cited

U.S. PATENT DOCUMENTS 3,850,577   11/1974   Ashkar ...................... 23/230 B

OTHER PUBLICATIONS

Rolleri et al., Clinca Chemica Acta, vol. 66, 1976, pp. 319-330.

*Primary Examiner*—Benjamin R. Padgett
*Assistant Examiner*—Christine M. Nucker
*Attorney, Agent, or Firm*—Robert J. Steinmeyer; Robert S. Frieman

[57] ABSTRACT

An in vitro radioimmunoassay procedure for measuring an amount of steroid in a sample wherein a separate serum protein inactivation step is eliminated. The separate protein serum inactivation step is eliminated by employing a solution wherein the solvent comprises from about 0 to about 10% of a water miscible organic solvent and from about 90 to about 100% of a buffer having a pH of from about 3 to about 6.

20 Claims, No Drawings

RADIOIMMUNOASSAY OF PLASMA STEROIDS

BACKGROUND OF THE INVENTION

1. Field of the Invention

This invention pertains to the in vitro radioimmunoassay of steroids present in serum.

2. Description of the Prior Art

Plasma steroid hormone clinical assay procedures often require time consuming, expensive, and precise laboratory manipulations. Plasma steroids have been measured by colorimetric (R. H. Silber and C. C. Porter, *J. Biol. Chem.*, 210:923-932 (1954)), fluorimetric (D. J. Mattingly, *J. Clin. Pathol.*, 15:374-378 (1962)), competitive protein binding (B. E. P. Murphy, *J. Clin. Endocrinol. Metab.*, 28:343 et seq. (1968)), and radioimmunoassay (R. W. Farmer and C. E. Pierce, *Clin. Chem.*, 20:411-414 (1974)) procedures, after organic solvent extraction. Any improvement of the assay procedure through the elimination of the preliminary extraction step is faced with the problem beset by the presence in the samples of carrier proteins competing with the antibodies. E. Rulleri, M. Zannino, S. Orlandini, and R. Malvano, Direct Radioimmunoassay of Plasma Cortisol, *Clinica Chemica Acta*, 66:319 to 330 (1976), point out "that direct assays in unextracted plasma have been reported, in which different techniques were adopted to circumvent protein effects, such as heat denaturation, incubation in an ethnolic medium, compensation for the protein content of samples, and protein inhibition by competition with massive amounts of steroids weakly cross-reacting with antibodies." However, these direct assay procedures still entail the use of a preliminary step prior to contacting the sample with the labeled steroid and antibody.

SUMMARY OF THE INVENTION

The present invention pertains to an in vitro radioimmunoassay procedure wherein the preliminary serum protein inactivation step is eliminated. The in vitro radioimmunoassay procedure of this invention comprises simultaneously inactivating serum proteins while labeled and unlabeled steroids compete for binding sites on steroid specific binders. This simplified procedure is accomplished by contacting the sample with a solution comprising a solvent and a solute, said solute comprising labeled steroids and binders specific for said steroids, and said solvent comprising from about 0 to about 10% of a water miscible organic solvent and from about 90 to about 100% of a buffer having a pH of from about 3 to about 6; separating binder bound steroids from unbound steroids into two fractions; and measuring one of said fractions for the presence of labeled steroids.

DESCRIPTION OF THE PREFERRED EMBODIMENTS

Conventional in vitro radioimmunoassay procedures for measuring the steroid level in a sample comprise four basic steps. These steps are: (1) inactivating serum proteins in a sample to be determined; (2) contacting and incubating the sample comprising the inactivated serum proteins and steroids to be measured with a solution comprising a solvent and a solute, said solute comprising labeled steroids and specific binders for said steroids; (3) separating the bound steroids from the unbound steroids into two portions; and (4) measuring either portion for the presence of labeled steroids. An alternative conventional method employs an additional step between steps 1 and 2, which additional step entails removing the inactivated serum proteins from the sample prior to contacting the sample with the solution.

One or more types of binders which are specific for the steroid being assayed can be present in the solution. The steroid specific binders can be either antibodies or proteins. Preferably, the steroid specific binders are antibodies. In contrast to the binders, only one type of labeled steroid is present in the solution.

The heart and essence of the present invention is the elimination of the separate serum protein inactivation step as well as the elimination of the optional protein separation step. It has been discovered that by using a solution wherein the solvent comprises from about 0 to about 10% of a water miscible organic solvent and from about 90 to about 100% of a buffer having a pH of from about 3 to about 6, steps (1) and (2), supra, can be performed simultaneously, thereby eliminating one or two steps of the procedure with a corresponding savings in time without sacrificing the efficacy or accuracy of the diagnostic test. Preferably, the solvent comprises from about 3 to about 7% of said organic solvent and from about 93 to about 97% of said buffer. More preferably, the solvent comprises about 5% of said organic solvent and about 95% of said buffer.

The organic solvent can be any organic solvent which is miscible in water. Organic solvents which can be used in the present invention include methanol, ethanol, dioxane, acetone, dimethyl formamide, ethylene glycol, and propylene glycol. Preferably, the organic solvent is selected from a group consisting of methanol and ethanol.

The buffer can be any buffer having a pH from about 3 to about 6. Preferred buffers have a pH range of from about 4 to about 5.

Exemplary buffers which can be used in the present invention include a metal salt of acetic acid, a metal salt of citric acid, a metal salt of maleic acid, glutamate-acetate, glutamate-citrate, glutamate-hydrogen chloride, glycinate-hydrogen chloride, and glycinate-phosphate. Virtually any metal salt can be used. Exemplary metal salts which can be used in the present invention include alkali metal salts. Preferred metal salts are sodium and potassium salts. Sodium citrate and sodium acetate are the preferred buffers.

Although the final sample dilution in the reaction mixture is not critical, it is preferred to have the sample and solution present in amounts such that the sample has a final sample dilution of from about 1/10 to about 1/100 and more preferably from about 1/25 to about 1/50.

When the solvent comprises from about 0 to about 3 percent of said water miscible organic solvent and from about 97 to about 100 percent of said buffer, it is preferred, but not essential, that said buffer have a pH of from about 3 to about 5.

The above, as noted, describe the essentials of the present invention. Steps (3) and (4) of the in vitro radioimmunoassay procedure for measuring the steroid level in a sample can be performed by any method known to those skilled in the art.

Various separation techniques which can be employed in step (3) to separate the bound from the free steroids are disclosed in J. G. Ratcliffe, Separation Techniques in Saturation Analysis, *Br. Med. Bull.*, 30(1):32 to 37 (1974), said article being incorporated herein in toto by reference.

Either or both fractions can be measured for the presence of labeled steroids, i.e., step (4) can be performed, by using either a gamma counting or liquid scintillation counting system. As known to those skilled in the art, a liquid scintillation counting system generally is used to assay a tritium or radiocarbon labeled substance while a gamma counting system entails the use of a gamma ray emitting substance, e.g., $I^{125}$, $Se^{75}$, etc. Because of the lower cost involved, gamma counting techniques are usually preferred. It is also preferred to use $I^{125}$ as the label.

The simplified radioimmunoassay procedure of the present invention can be employed to quantitatively or qualitatively measure the amount of any steroid in a sample. Gonadal and adrenal steroid hormones are exemplary steroids which can be measured by the present invention. Preferably, this invention can be used to measure estrogens, progesterons, androgons, mineral corticoids and glucocorticoids. More preferably this invention can be employed to measure cortisol, estriol and aldosterone. The measurement of cortisol and estriol by the simplified procedure of this invention is of particular importance because of their frequent diagnosis in clinical laboratories.

The antibodies used in the present invention can be present either in solution or bound to a solid phase by any physical or chemical means known to those skilled in the art.

Tfhe following examples are provided for the purpose of further illustration only and are not intended to be limitations on the disclosed invention.

EXAMPLE 1

Protocol for Cortisol Test

Lyophilized $^{125}I$-labeled hydrocortisone cortisol labeled with less than 3 microcuries of $^{125}I$ is reconstituted with 10 ml of 5 percent methanol in sterile distilled water. The solution is swirled gently to mix and then allowed to stand for thirty minutes before using. After reconstitution, the reagent is clear and colorless.

Lyophilized cortisol antiserum (rabbit) to cortisol is reconstituted with 10 ml of 5 percent methanol in sterile distilled water. This solution is also gently swirled to mix and then allowed to stand for thirty minutes before using. After reconstitution, the reagent is clear and colorless.

Lyophilized cortisol precipitating antibody (goat-anti-rabbit gamma globulin) is also reconstituted with 10 ml of 5 percent methanol in sterile distilled water. The solution is then swirled to mix and allowed to stand for thirty minutes before using. If a precipitate is present immediately after reconstitution, the solution should be vortex mixed for 5 to 10 seconds. The vortex mixing will result in the precipitate going back into solution.

When reconstituted according to the preceding direction, each one of the above 3 reagents will also contain the following:
 a. 0.025 molar sodium citrate
 b. 0.10 molar sodium chloride
 c. 0.005 molar ethylenediaminetetraacetic acid
 d. 0.1 percent gelatin
 e. 0.1 percent bovine serum albumin
 f. 0.01 percent sodium azide as a preservative Lyophilized cortisol buffer is reconstituted with 5 ml of sterile distilled water. The solution is swirled gently to mix and let stand for thirty minutes before using. After reconstitution, the reagent is clear and colorless.

After reconstitution the buffer comprises 0.01 molar phosphate, 0.15 molar sodium chloride, 0.005 molar ethylenediaminetetraacetic acid, 0.1 percent gelatin, 3.5 percent bovine serum albumin, and 0.01 percent sodium azide as a preservative.

Six lyophilized cortisol standards, prepared in the buffer described above, are reconstituted with 2 ml of sterile distilled water and allowed to stand for 15 to 30 minutes without mixing. After reconstitution, each standard contains 0.01 percent sodium azide as a preservative and is free of any precipitate. Each standard is swirled before use. The cortisol concentrations of the six reconstituted standards is shown in Table I.

TABLE I

| Cortisol Standard | Cortisol Concentrations | |
|---|---|---|
| | μg/dl | nmol/l |
| A | 1 | 28 |
| B | 2 | 55 |
| C | 5 | 138 |
| D | 10 | 280 |
| E | 20 | 550 |
| F | 50 | 1380 |

A lyophilized cortisol control serum containing a known amount of cortisol in human defibrinated plasma is reconstituted with 2 ml of sterile distilled water and allowed to stand for 15 30 minutes without mixing. After reconstitution the cortisol serum contains 0.01 percent sodium azide as a preservative and is free of any precipitate. The reconstituted control serum is gently swirled before use.

The precipitating antibody is combined with the $^{125}I$-cortisol by transferring the precipitating antibody solution into a vial containing the $^{125}I$-cortisol. The combined solution is mixed thoroughly.

Using the above reagents the following assay protocol is followed.

ASSAY PROTOCOL

1. Label 20 tubes in duplicate as follows: T.C., blank, $B_o$, A through F, and CS (control serum). Label two tubes, in duplicate, for each patient serum sample.
2. Add 200 μl sterile distilled water to blank tubes.
3. Add 20 μl of buffer to the $B_o$ tubes.
4. Add 20 μl of standards A through F to the appropriate tubes.
5. Add 20 μl of control serum to CS tubes.
6. Add 20 μl of each patient's serum to the appropriate tubes.
7. Add 400 μl of the $^{125}I$-cortisol-precipitating antibody mixture to all tubes. Immediately before use, vortex mix the mixture for 5 to 10 seconds. Cap T.C. tubes and set aside.
8. Add 200 μl of dilute cortisol antiserum to all tubes except T.C. and blank. Cap all tubes and mix by gentle swirling or gentle vortexing.
9. Incubate for 2 hours at 37° C (except T.C. tubes).
10. Add 1 ml cold (2° C to 8° C) saline to each tube (except T.C.) and cap tubes.
11. Immediately centrifuge all tubes (except T.C.) for 15 minutes at a minimum of 1500 × g.
12. Carefully decant each tube (except T.C.) and discard supernatant.

After decanting, gently blot the remaining supernatant which rims the top of the tube against plastic-backed absorbent paper. Cap all tubes.

13. Count all tubes, including T.C., for a length of time to give reasonable counting statistics for each tube (e.g., 10,000 counts gives 26 counting error of 2%). This should be between 1 and 10 minutes.

As known to those skilled in the art, there are several methods used to plot standard curves and obtain the concentration of serum constituent. Methods used include: B/T or $B/B_o$ versus concentration or log concentration, T/B versus concentration, or logit $B/B_o$ versus log concentration. The plot of B/T versus log concentration is convenient for hand calculations. This method is explained as follows:

1. Use the following formula to calculate the amount of labeled cortisol bound to anti-cortisol in the absence of any unlabeled cortisol.

$$\%B_o = \frac{B_o \text{ counts} - \text{blank}}{T.C. \text{ counts} = \text{blank}} \times 100$$

2. Determine the amount of labeled cortisol bound to anti-cortisol in standard and patient sample vials as follows:

$$\%B = \frac{B \text{ counts for standard or patient sample} - \text{blank}}{T.C. \text{ counts} - \text{blank}} \times 100$$

3. Plot %B values of standards against μg/dl cortisol on two-cycle semilogarithmic graph paper with μg/dl cortisol on the log scale.

4. Determine the concentrations of cortisol in patient sample and control serum from the standard curve.

EXAMPLE 2

Twenty-two serum samples were assayed for cortisol by both the procedure of Example 1, i.e., an exemplary radioimmunoassay procedure (RIA) within the scope of this invention, and the competitive protein binding (CPB) procedure discussed by B. E. P. Murphy, *J. Clin. Endocrinol. Metab.*, 28:343 et seq. (1968), said publication being incorporated herein in toto by reference. The results obtained from these assays are listed in Table II.

TABLE II

| Sample | RIA-$^{125}$I μg/dl | CPB-$^3$H μg/dl |
|---|---|---|
| 1 | 5.28 | 2.5 |
| 2 | 13.13 | 8.2 |
| 3 | 8.12 | 4.5 |
| 4 | 17.96 | 11.6 |
| 5 | 15.71 | 9.1 |
| 6 | 8.21 | 3.0 |
| 7 | 22.02 | 14.1 |
| 8 | 16.40 | 11.0 |
| 9 | 23.90 | 17.4 |
| 10 | 35.39 | 28.5 |
| 11 | 12.23 | 12.5 |
| 12 | 44.10 | 35.0 |
| 13 | 25.82 | 20.5 |
| 14 | 10.66 | 4.6 |
| 15 | 24.29 | 21.0 |
| 16 | 30.59 | 27.5 |
| 17 | 5.01 | 3.5 |
| 18 | 27.09 | 21.0 |
| 19 | 10.09 | 7.0 |
| 20 | 25.95 | 24.5 |
| 21 | 16.02 | 12.5 |
| 22 | 4.91 | 3.5 |

The data of Table II when subjected to the standard method of least squares produced the following equation:

RIA = 1.14 CPB + 0.49

The recovery from Murphy's CPB procedure is approximately 85 percent. Therefore, the fact that the present invention's RIA procedure shows recovery values approximately 14 percent higher than the recovery values obtained via Murphy's CPB procedure indicates that the present invention's RIA procedure comes closer to measuring the total amount of cortisol in a patient's serum.

The above data generates a correlation coefficient of 0.988. This correlation coefficient indicates a linear relationship between the two assay procedures.

EXAMPLE 3

The procedure of Example 1 was used in the following assays to determine the percent recovery obtained via the modified RIA method of the disclosed invention. First a serum sample was assayed for cortisol. Spectrophotometrically assayed cortisol was then added to this serum sample in the quantities indicated in Table III. These samples were then reassayed and the data obtained are also listed in Table III.

TABLE III

| | Cortisol RIA Recovery | | |
|---|---|---|---|
| Cortisol Added (μg/dl) | Cortisol Found (μg/dl) | Cortisol Found (μg/dl) | Recovery (1) |
| 0 | 6.8 | — | — |
| 5.6 | 12.8 | 12.4 | 106 |
| 22.3 | 30.6 | 29.1 | 106 |

The percent recovery shown in Table III clearly indicates that while one or more steps have been eliminated from the prior art RIA method, the function of these steps has been retained in the present invention and the present invention can, in fact, be used to give quantitative results of serum steroids.

Based on this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. An in vitro radioimmunoassay procedure comprising:
   (a) contacting a sample comprising serum proteins and steroids with a solution comprising a solvent and a solute, said solute comprising labeled steroids and specific binders for said steroids, and said solvent comprising from about 0 to about 10% by weight of a water miscible organic solvent and from about 90 to about 100% of a buffer having a pH of from about 3 to about 6, whereby the serum proteins are simultaneously inactivated while labeled and unlabeled steroids compete for binding sites on said steroid specific binders;
   (b) separating bound steroids from unbound steroids into two fractions; and
   (c) measuring one of said fractions for the presence of labeled steroids.

2. The procedure of claim 1 wherein said labeled steroids are labeled cortisol.

3. The procedure of claim 1 wherein said solvent comprises from about 3 to about 7 percent of said water miscible organic solvent and from about 93 to about 97 percent of said buffer having a pH of from about 4 to about 5.

4. The procedure of claim 3 wherein said labeled steroids are labeled cortisol.

5. The procedure of claim 1 wherein said sample and solution are present in amounts such that said sample has a final sample solution of from about 1/10 to about 1/100.

6. The procedure of claim 5 wherein said labeled steroids are labeled cortisol.

7. The procedure of claim 5 wherein said solvent comprises from about 3 to about 7 percent of said water miscible organic solvent and from about 93 to about 97 percent of said buffer having a pH of from about 4 to about 5.

8. The procedure of claim 7 wherein said labeled steroids are labeled cortisol.

9. The procedure of claim 7 wherein said organic solvent is selected from a group consisting of methanol, ethanol, dioxane, acetone, dimethyl formamide, ehtylene glycol and propylene glycol, and wherein said buffer is selected from a group consisting of a metal salt of acetic acid, a metal salt of citric acid, a metal salt of maleic acid, glutamate-acetate, glutamate-citrate, glutamate-hydrogen chloride, glycinate-hydrogen chloride, and glycinate-phosphate.

10. The procedure of claim 9 wherein said labeled steroids are labeled cortisol.

11. The procedure of claim 9 wherein said organic solvent is selected from the group consisting of methanol and ethanol and wherein said buffer is selected from a group consisting of sodium citrate and sodium acetate.

12. The procedure of claim 11 wherein said labeled steroids are labeled cortisol.

13. The procedure of claim 11 wherein said solvent comprises about 5% of said organic solvent and about 95% of said buffer.

14. The procedure of claim 13 wherein said labeled steroids are labeled cortisol.

15. The procedure of claim 13 wherein said sample and solution are present in amounts such that said sample has a final sample dilution of from about 1/25 to about 1/50.

16. The procedure of claim 15 wherein said labeled steroids are labeled cortisol.

17. The procedure of claim 1 wherein said solvent comprises from about 0 to about 3 percent of said water miscible organic solvent and from about 97 to about 100 percent of said buffer having a pH of from about 3 to about 5.

18. The procedure of claim 17 wherein said labeled steroids are labeled cortisol.

19. The procedure of claim 17 wherein said sample and solution are present in amounts such that said sample has a final sample dilution of from about 1/10 to about 1/100.

20. The procedure of claim 19 wherein said labeled steroids are labeled cortisol.

* * * * *